United States Patent [19]

Schmolka

[11] Patent Number: 4,490,279
[45] Date of Patent: Dec. 25, 1984

[54] FOAM-STABILIZED COMPOSITIONS

[75] Inventor: Irving R. Schmolka, Grosse Ile, Mich.

[73] Assignee: BASF Wyandotte Corporation, Wyandotte, Mich.

[21] Appl. No.: 293,100

[22] Filed: Aug. 17, 1981

Related U.S. Application Data

[63] Continuation-in-part of Ser. No. 85,885, Oct. 17, 1979, abandoned.

[51] Int. Cl.$^3$ .................. B01F 17/16; C11D 1/75
[52] U.S. Cl. .................... 252/357; 252/307; 252/547; 252/DIG. 1; 252/DIG. 5; 252/DIG. 10; 252/DIG. 13
[58] Field of Search ......... 252/357, 307, 547, DIG. 1, 252/DIG. 3

[56] References Cited

U.S. PATENT DOCUMENTS

| | | | |
|---|---|---|---|
| 3,202,714 | 8/1965 | Zimmerer et al. | 252/547 X |
| 3,402,128 | 9/1968 | Puchta et al. | 252/547 X |
| 3,843,563 | 10/1974 | Davies et al. | 252/547 |
| 4,026,825 | 5/1977 | Steen et al. | 252/551 X |

OTHER PUBLICATIONS

Schick: "Nonionic Surfactants", Marcel Dekker, Inc., New York (1966), pp. 408 and 409.
Schwartz et al.: "Surface Active Agents and Detergents", vol. II, Robert E. Krieger Publ. Co., Huntington, N.Y. (1977), pp. 551-552.

*Primary Examiner*—Richard D. Lovering
*Attorney, Agent, or Firm*—Joseph D. Michaels

[57] ABSTRACT

The invention relates to foam stabilized compositions containing (a) a high foaming nonionic surfactant which is a block copolymer that is an alkylene oxide adduct of ethylene glycol, propylene glycol, or diethylene glycol, and (b) a foam-stabilizing amount of an amine oxide derived from a fatty alcohol which has been oxyethylated to the extent that ethylene oxide units account for approximately 50 to 75 weight percent of the molecular weight of the fatty alcohol-ethylene oxide adduct. The compositions are useful in the formulation of various products in which foam stability is needed, such as hand detergent bars, hair shampoos, rug shampoos, hand dishwashing detergents, etc..

7 Claims, No Drawings

FOAM-STABILIZED COMPOSITIONS

CROSS-REFERENCE TO RELATED APPLICATION

This application is a continuation-in-part of application, Ser. No. 85,885, filed on Oct. 17, 1979, now abandoned.

BACKGROUND OF THE INVENTION

1. Field of the Invention

This invention relates to compositions of matter containing certain nonionic surfactants and certain amine oxides. The compositions are high foamers and have good foam stability.

2. Description of the Prior Art

A wide variety of amine oxides are known in the art. See for example U.S. Pat. Nos. 3,402,128, 3,666,632, and 3,202,714. It is also known that amine oxides can be added to nonionic surfactants to effect their foam properties.

Although such general teachings are known, it is difficult to find specific combinations of amine oxides and nonionic surfactants which are suitable for specific applications. Whether particular combinations will be effective for specific purposes is highly unpredictable.

One area of concern involves attempts to stabilize high foaming nonionic surfactants. High foaming surfactants are needed for a variety of applications such as for dishwashing detergents, hair shampoos, rug shampoos, and hand detergents. The problem with many of the high-foaming nonionic surfactants, however, is that the foam is not stable for long periods of time. Consequently, there is a need to find ways of stabilizing the foam in high foaming nonionic surfactants.

SUMMARY OF THE INVENTION

The subject invention relates to compositions comprising (a) a high foaming nonionic surfactant, said nonionic surfactant being a block copolymer which is an alkylene oxide adduct of ethylene glycol, propylene glycol, or diethylene glycol and (b) a foam-stabilizing amount of an amine-oxide having the formula

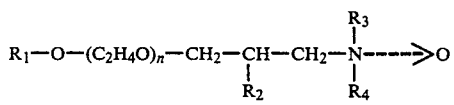

wherein $R_1$ is a linear alkyl group having 10 to 20 carbon atoms, $R_2$ is hydrogen or hydroxyl, $R_3$ and $R_4$ are 2-hydroxyalkyl groups containing 2 to 4 carbon atoms, and n is a number such that from 50–75 percent of the weight of the radical $R_1-O(C_2H_4O)_n-$ is attributable to ethylene oxide units.

The compositions are high foaming and the foam stability is maintained for extended periods of time. The compositions are useful as ingredients in dishwashing detergents, hair shampoos, rug shampoos, and hand detergents.

DESCRIPTION OF THE PREFERRED EMBODIMENT

The nonionic surfactants which are used in the subject invention are high foaming block copolymers that are alkylene oxide adducts of ethylene glycol, propylene glycol or diethylene glycol. As used herein, a high foaming nonionic surfactant is one which will reach a foam height of 600 mm within 10 minutes at a flow rate of 400 ml per minute when tested with a dynamic foam machine such as the one described by Reich et al in *Soap and Chemical Specialties*, Vol. 37, page 55 (April, 1961). Those of ordinary skill in the art will know which block copolymers that are alkoxylation products of ethylene glycol or propylene glycol are high foamers. They will also know how to prepare such surfactants. For specific information on their preparation, see U.S. Pat. Nos. 2,674,619 and 2,677,700. The amount of nonionic surfactant used is from 0.5 to 50 percent by weight based on the total weight of the composition.

The amine-oxide foam-stabilizing agents used in accordance with this invention have the structural formula

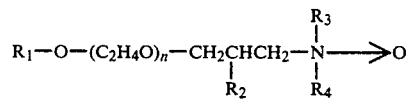

wherein $R_1$ is a linear alkyl group having 10 to 20 carbon atoms, $R_2$ is hydrogen or hydroxyl, and $R_3$ and $R_4$ are 2-hydroxyalkyl groups containing 2 to 4 carbon atoms, and n is a number such that from 50–75 percent of the weight of the radical $R_1-O(C_2H_4O)_n-$ is attributable to ethylene oxide units. The method of making the amine oxides used in the invention is well known in the art. For specific details, see U.S. Pat. Nos. 3,402,128 and 3,366,632.

The amount of amine oxide used is defined functionally as a foam-stabilizing amount. For the purposes of the present invention, the term "foam-stabilizing amount" may be defined as one not exceeding 10 percent by weight of the high foaming nonionic surfactant present, and an amount sufficient, in a foam-stability test, to prevent a collapse of foam height of greater than 50 percent during a ten minute wait. However, it is usually preferred that sufficient amine oxide be used to prevent the observed foam height from collapsing by more than 20 percent. Generally from 0.5 to 6 percent by weight of amine oxides, relative to the weight of the high foaming nonionic surfactant, will be sufficient to satisfy the requirements.

The compositions of this invention may also contain other ingredients such as other surfactants, abrasives, fillers, dyes, perfumes, soil anti-redeposition agents, optical brighteners, etc.

The examples which follow will illustrate in more detail the practice of this invention. In the examples which follow, the following abbreviations will be used:

$S_1$ —a nonionic surfactant which is a block copolymer prepared by using propylene glycol as an initiator; said surfactant contains an internal block of propylene oxide units and external blocks of ethylene oxide units, wherein the typical molecular weight attributable to the polyoxypropylene hydrophobe is 1750 and the proportion of polyoxyethylene hydrophilic units in the total molecule is approximately 80 percent.

$S_2$ —a nonionic surfactant which is a block copolymer prepared by using propylene glycol as an initiator; said surfactant contains an internal block of propylene oxide units and external blocks of ethylene oxide units wherein the typical molecular weight attributable to the polyoxypropylene hydrophobe is 2,250 and the proportion of polyoxyethylene hydrophilic units in the total molecule is approximately 70 percent.

$S_3$ —a nonionic surfactant which is a block copolymer prepared by using propylene glycol as an initiator; said surfactant contains an internal block of propylene oxide units and external blocks of ethylene oxide units wherein the typical molecular weight attributable to the polyoxypropylene hydrophobe is 3,250 and the proportion of polyoxyethylene hydrophilic units in the total molecule is approximately 50 percent.

$C_1$ —a comparative nonionic surfactant which is a block copolymer prepared by using N,N'-tetrakis-2-hydroxypropyl(ethylenediamine) as an initiator; said surfactant contains internal blocks of propylene oxide units and external blocks of ethylene oxide units wherein the typical molecular weight attributable to the polyoxypropylene hydrophobe is from 2,501–3000 and the proportion of polyoxyethylene hydrophilic units in the total molecule is approximately 40 percent.

$C_2$ —a comparative nonionic surfactant prepared by adding 27 moles of ethylene oxide to one mole of a mixture of cetyl and stearyl alcohol.

$C_3$ —a comparative nonionic surfactant which is a block copolymer prepared by using propylene glycol as an initiator; said surfactant contains an internal block of propylene oxide units and external blocks of ethylene oxide units wherein the typical molecular weight attributable to the polyoxypropylene hydrophobe is 950 and the proportion of polyoxyethylene hydrophilic units in the total molecule is approximately 50 percent.

$A_1$ —is a product made by oxyethylating a C straight-chain alkanol to give an adduct in which oxyethylene units account for approximately 62 percent of the total molecular weight, followed by reaction with epichlorohydrin, diethanolamine, and hydrogen peroxide.

$A_2$ —an amine oxide prepared for comparative purpose; the amine oxide is prepared in the same manner as $A_1$ except propylene oxide is used instead of ethylene oxide.

In Examples 1–3 which follow, a nonionic surfactant and $A_1$ were combined and diluted with water. The ingredients used and the concentrations are provided in Table I which follows. The foaming power and stability of the compositions was measured by using a dynamic foam machine such as the one described by Reich et al, *Soap and Chemical Specialties*, Vol. 37, page 55 (April, 1961). The results of these tests are also given in Table I. The table shows that foam height was measured using a 400 mm per minute flow. The reading before the slash shows the maximum foam height achieved while the reading after the slash shows the foam height 10 minutes after the maximum foam height has been achieved. The maximum reading was that which was achieved during a wait of no more than 10 minutes. The maximum reading reflects the foaming power of the surfactant. By comparing this reading with the reading after a ten minute wait, one can determine the amount of collapse. The less collapse, the greater the foam stability.

For comparison purposes, the table also shows the foam data for $A_1$, $S_1$, $S_2$, and $S_3$ alone. These comparative examples are designated $A_1$, $S_1$, $S_2$, and $S_3$ respectively. The data show that combining $A_1$ with $S_1$, $S_2$, and $S_3$ will stabilize the foam of $S_1$, $S_2$, and $S_3$.

TABLE I

| | | | Examples 1–3 | | | | |
|---|---|---|---|---|---|---|---|
| | $A_1$ | $S_1$ | 1 | $S_2$ | 2 | $S_3$ | 3 |
| Ingredient | | | | | | | |
| Water | 100 | 100 | 100 | 100 | 100 | 100 | 100 |
| $A_1$ | 0.002 | — | 0.002 | — | 0.002 | — | 0.002 |
| $S_1$ | — | 0.1 | 0.1 | — | — | — | — |
| $S_2$ | — | — | — | 0.1 | 0.1 | — | — |
| $S_3$ | — | — | — | — | — | 0.1 | 0.1 |
| Foam Height | | | | | | | |
| 400 ml (rate) | 90/80 | 600/130 | 600/550 | 600/100 | 600/550 | 600/480 | 600/500 |

For comparison purposes $A_1$ was tested with several other high foaming nonionic surfactants to determine whether $A_1$ acted as a foam stabilizer. The results are summarized in Table II which follows. The table shows the foam data for $C_1$, $C_2$, and $C_3$ without the addition of $A_1$. It also shows the foam data for mixtures of $A_1$ with $C_1$, $C_2$, and $C_3$. The data for the mixtures are provided under $C_1A_1$, $C_2A_1$, and $C_3A_1$ of the table. Table II indicates that $A_1$ does not act as a suitable foam stabilizer for these surfactants.

TABLE II

| | | | Example 4 | | | |
|---|---|---|---|---|---|---|
| | $C_1$ | $C_1A_1$ | $C_2$ | $C_2A_1$ | $C_3$ | $C_3A_1$ |
| Ingredient | | | | | | |
| Water | 100 | 100 | 100 | 100 | 100 | 100 |
| $A_1$ | — | 0.002 | — | 0.002 | — | 0.002 |
| $C_1$ | 0.1 | 0.1 | — | — | — | — |
| $C_2$ | — | — | 0.1 | 0.1 | — | — |
| $C_3$ | — | — | — | — | 0.1 | 0.1 |
| Foam Height | | | | | | |
| at 400 ml | 600/200 | 600/150 | 600/300 | 600/330 | 45/<10 | 550/200 |

For comparison purposes, another amine oxide $A_2$ was used in combination with $S_1$, $S_2$, and $S_3$. $A_2$ is similar to $A_1$ except that it contains 62 percent propylene oxide units instead of ethylene oxide units. Table III gives the foam data for $A_2$ alone and the foam data for the combinations of $A_2$ with $S_1$, $S_2$ and $S_3$ Table III read in conjunction with Table I shows that $A_2$ is not as effective as $A_1$ at stabilizing the foam produced by $S_1$, $S_2$, and $S_3$.

TABLE III

|  | Example 5 | | | |
| --- | --- | --- | --- | --- |
| Ingredient | $A_2$ | $S_1A_2$ | $S_2A_2$ | $S_3A_2$ |
| Water | 100 | 100 | 100 | 100 |
| $A_1$ | 0.002 | 0.002 | 0.002 | 0.002 |
| $S_1$ | — | 0.1 | — | — |
| $S_2$ | — | — | 0.1 | — |
| $S_3$ | — | — | — | 0.1 |
| Foam Height | | | | |
| at 400 ml | 20/10 | 600/500 | 600/170 | 600/430 |

The embodiments of this invention in which an exclusive property or privilege is claimed are defined as follows:

1. A composition consisting essentially of (a) a nonionic surfactant which is a block copolymer that is an alkylene oxide adduct of ethylene glycol, propylene glycol, or diethylene glycol, and (b) a foam-stabilizing amount of an amine oxide having the formula

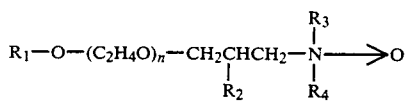

wherein $R_1$ is a linear alkyl group having 10 to 20 carbon atoms, $R_2$ is hydrogen or hydroxyl, and $R_3$ and $R_4$ are 2-hydroxyalkyl groups containing 2 to 4 carbon atoms, and n is a number such that from 50–75 percent of the weight of the radical $R_1$—O—$(C_2H_4O)_n$— is attributable to ethylene oxide units.

2. A composition as defined in claim 1, wherein $R_1$ is $C_{14}H_{29}$—, $R_2$ is hydroxyl, and $R_3$ and $R_4$ are each 2-hydroxyethyl, and n has a value of about 8 to 9.

3. A composition as defined in claim 2, wherein the amount of amine-oxide present is from 1 to 6 percent by weight, relative to the weight of the high foaming nonionic surfactant.

4. A composition as defined in claim 1, wherein the amount of amine-oxide present is from 1 to 6 percent by weight, relative to the weight of high foaming nonionic surfactant.

5. A composition as defined in claim 3 or 4 wherein the amount of amine oxide present is 2 percent by weight, relative to the weight of high foaming nonionic surfactant.

6. A method of improving the foam stability of a high foaming nonionic surfactant which is a block copolymer that is an alkylene oxide adduct of ethylene glycol, propylene glycol, or diethylene glycol which comprises adding thereto from 1 to 6 percent by weight of an amine-oxide having the structural formula

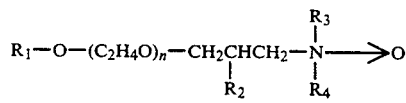

wherein $R_1$ is a linear alkyl group having 10 to 20 carbon atoms, $R_2$ is hydrogen or hydroxyl, $R_3$ and $R_4$ are 2-hydroxyl groups containing 2 to 4 carbon atoms, and n is a number such that from 50–75 percent of the weight of the radical $R_1$—O—$(C_2H_4O)_n$— is attributable to ethylene oxide units.

7. A method as defined in claim 6, wherein $R_1$ is $C_{14}H_{29}$—, $R_2$ is hydroxyl, and $R_3$ and $R_4$ are each 2-hydroxyethyl, and n has a value of about 8 to 9.

* * * * *